(12) United States Patent
Decouteau et al.

(10) Patent No.: US 9,800,582 B2
(45) Date of Patent: Oct. 24, 2017

(54) METHOD AND APPARATUS GENERATING AND APPLYING SECURITY LABELS TO SENSITIVE DATA

(71) Applicant: EDMOND SCIENTIFIC COMPANY, Chantilly, VA (US)

(72) Inventors: Duane Decouteau, Missoula, MT (US); John Pitale, Fairfax Station, VA (US)

(73) Assignee: EDMOND SCIENTIFIC COMPANY, Chantilly, VA (US)

( * ) Notice: Subject to any disclaimer, the term of this patent is extended or adjusted under 35 U.S.C. 154(b) by 0 days.

(21) Appl. No.: 14/293,651

(22) Filed: Jun. 2, 2014

(65) Prior Publication Data
US 2015/0020213 A1    Jan. 15, 2015

Related U.S. Application Data

(60) Provisional application No. 61/831,059, filed on Jun. 4, 2013.

(51) Int. Cl.
| | |
|---|---|
| *H04L 29/06* | (2006.01) |
| *H04L 29/08* | (2006.01) |
| *G06Q 50/26* | (2012.01) |
| *G06F 19/00* | (2011.01) |
| *G06F 21/62* | (2013.01) |

(52) U.S. Cl.
CPC ............ *H04L 63/10* (2013.01); *G06F 19/322* (2013.01); *G06F 21/6245* (2013.01); *G06Q 50/265* (2013.01); *H04L 63/105* (2013.01); *H04L 67/12* (2013.01); *G06F 2221/2141* (2013.01); *H04L 63/20* (2013.01)

(58) Field of Classification Search
CPC ........ H04L 63/10; H04L 67/12; G06Q 50/265; G06F 19/322
USPC .......................................................... 726/27
See application file for complete search history.

(56) References Cited

U.S. PATENT DOCUMENTS

| | | | | |
|---|---|---|---|---|
| 5,899,998 | A  * | 5/1999  | McGauley et al. | 709/201 |
| 6,915,254 | B1 * | 7/2005  | Heinze et al. | 704/9 |
| 8,843,997 | B1 * | 9/2014  | Hare | 726/3 |
| 2006/0259977 | A1 * | 11/2006 | Patrick | G06F 21/6245 726/26 |
| 2006/0287890 | A1 * | 12/2006 | Stead et al. | 705/3 |
| 2007/0061393 | A1 * | 3/2007  | Moore | 709/201 |

(Continued)

OTHER PUBLICATIONS

HL7.org, "Introduction to HL7", Jul. 29, 2012, retrieved from https://web.archive.org/web/20120729032336/http://www.hl7.org/implement/standards/fhir/introduction.htm on Jun. 13, 2015.*

*Primary Examiner* — Matthew Henning
(74) *Attorney, Agent, or Firm* — Staas & Halsey LLP

(57) ABSTRACT

The disclosure comprises a method, an apparatus, and instructions for controlling a computer to implement a security labeling service (SLS) to tag an electronic record or data stream with security labels to ensure compliance with access restriction requirements. The SLS tags a record or data stream with security labels according to constraints including jurisdictional (government regulation), organizational policy, and authorization of a subject of record (e.g. patient consent). The SLS consumes a vocabulary dictionary to interpret the record and the constraints to generate rules for tagging the data. The original record or data stream is then tagged according to the rules. The tagged output is used to ensure compliance with the security labels.

29 Claims, 7 Drawing Sheets

(56) References Cited

U.S. PATENT DOCUMENTS

| | | | | |
|---|---|---|---|---|
| 2007/0192323 | A1* | 8/2007 | Miller | 707/9 |
| 2008/0147436 | A1* | 6/2008 | Ohlsson | 705/2 |
| 2009/0070103 | A1* | 3/2009 | Beggelman et al. | 704/9 |
| 2009/0228303 | A1* | 9/2009 | Faulkner et al. | 705/3 |
| 2009/0320093 | A1* | 12/2009 | Glazier | G06F 8/10 726/1 |
| 2010/0082652 | A1* | 4/2010 | Jones | G06Q 30/02 707/758 |
| 2010/0138241 | A1* | 6/2010 | Ruark et al. | 705/3 |
| 2010/0169966 | A1* | 7/2010 | Yalamanchi | G06F 21/6245 726/21 |
| 2011/0247081 | A1* | 10/2011 | Shelton | G06F 21/6218 726/28 |
| 2013/0024429 | A1* | 1/2013 | Raas | 707/689 |
| 2013/0167249 | A1* | 6/2013 | Birtwhistle | G06F 19/322 726/28 |
| 2014/0164044 | A1* | 6/2014 | DeRoller | 705/7.22 |

\* cited by examiner

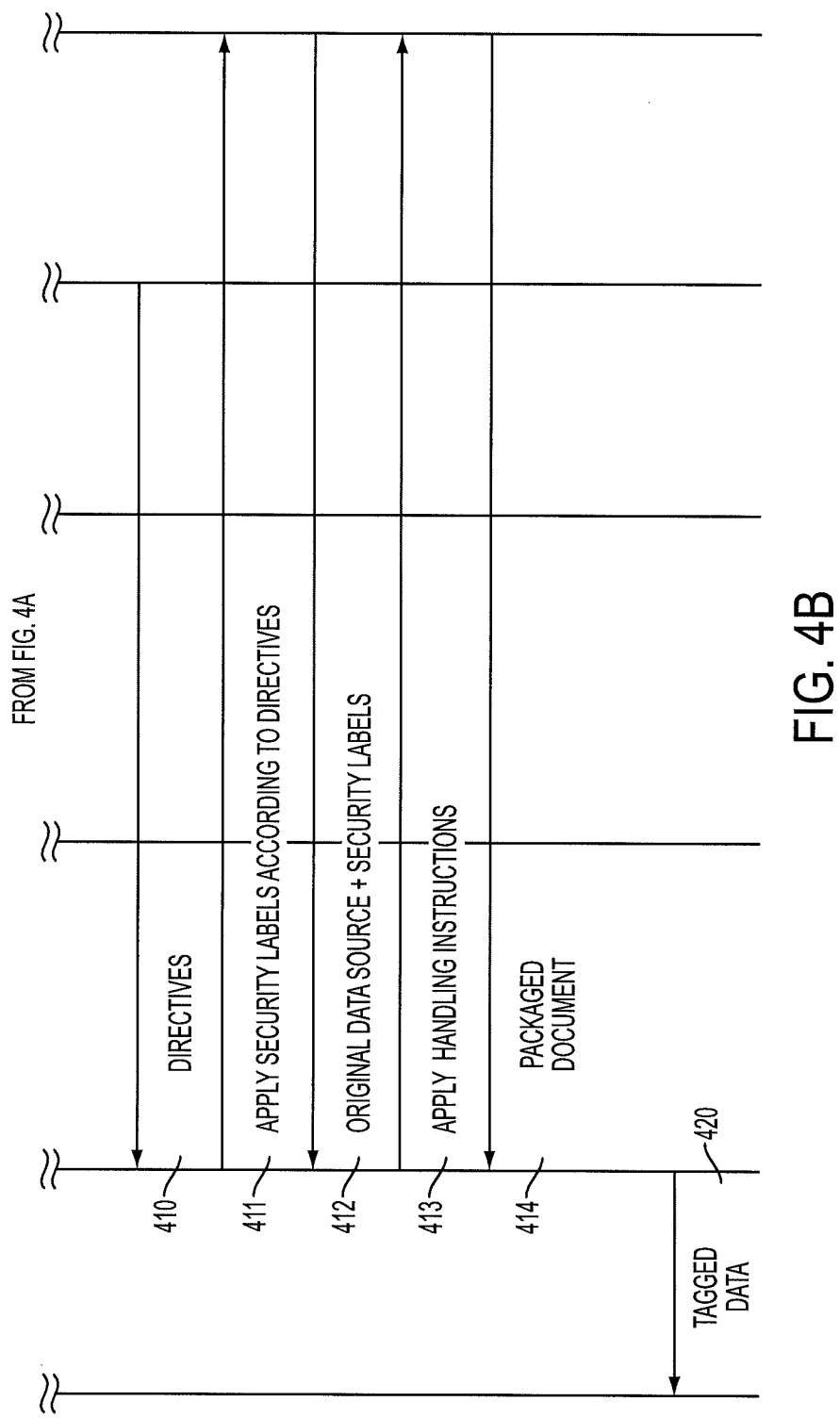

METHOD AND APPARATUS GENERATING AND APPLYING SECURITY LABELS TO SENSITIVE DATA

CROSS-REFERENCE TO RELATED APPLICATIONS

This application claims the benefit of U.S. Provisional Patent Application No. 61/831,059, filed on Jun. 4, 2013, in the United States Patent and Trademark Office, the disclosure of which is incorporated herein by reference.

BACKGROUND

1. Field

Example embodiments relate to a method, a computer-readable medium and an apparatus that may apply security labels to sensitive data based on authorization of a subject of record, organizational policies, and jurisdictional policies.

2. Description of the Related Art

Dissemination of sensitive data requires controlled, conditional access according to different levels or types of authorization. Examples of sensitive data include medical records, classified documents (e.g. DOD top secret), and the like. Access of such records may need to be limited according to both the sensitive nature of particular records as well as the purpose for requesting the records. For example, if a medical record contains data relating, e.g. HIV or psychiatric treatment, current Federal laws prohibit unrestricted distribution of such records, allowing access only in specific circumstances.

Enforcement of data handling requirements can become a problem upon records being transferred from an original custodian source. Once records are transferred, proper enforcement of data handling agreements or obligations may or may not occur. For example, medical records could be exchanged between service provider organizations. Once the records are transferred, it becomes difficult to police the handling of the data.

Solutions have been proposed based on maintaining separate databases for different versions of data, each with different levels of access privileges. One such example involves compiling the databases and subsequently providing access to the appropriate version of the data according to access rights. However, this method poses a new problem whenever access rights change. For example, if jurisdictional laws or regulations change to require different access rights to sensitive data, the entire database would need to be recompiled each time this occurs. This problem renders this particular method expensive, and potentially introduces down time when the databases are being recompiled.

Accordingly, there is a need for a solution that avoids maintaining separate databases and recompiling databases upon changes in access rights.

SUMMARY

Accordingly, one or more embodiments provide a method to tag at runtime an electronic record or an electronic data stream with a security label that enables automated compliance and enforcement with each of a subject of record authorization, an organizational policy, and a government regulation.

According to another aspect of an exemplary embodiment, the method may receive a retrieval request to retrieve an electronic record associated with a subject of record. The method may further determine a rule, by a computer, for tagging the electronic record based on a vocabulary dictionary, an authorization constraint, an organizational policy constraint, and a government rule constraint, where the authorization constraint is provided by the subject of record. The method may further retrieve the electronic record from a repository. The method may further decompose the electronic record into a decomposed data source. The method may further tag the electronic record at runtime with a security label according to the determined rule and the decomposed data source. The method may further transmit the tagged electronic record.

According to another aspect of an example embodiment, a Security Labeling Service (SLS) may be provided to tag the electronic record or electronic data stream. The SLS may comprise a rule generation service, an extraction engine, a rules engine, and a transformation engine. The rule generation service may generate rules using a vocabulary dictionary, decision considerations, and rule constraints. The extraction engine may decompose the electronic record or data stream into a decomposed data source. The rules engine may output a directive based on the rules from the rule generation service, the decomposed data from the extraction engine, and rule languages. The transformation engine may tag the electronic record or data stream using the directives from the rules engine.

Additional aspects, features, and/or advantages of exemplary embodiments will be set forth in part in the description which follows and, in part, will be apparent from the description, or may be learned by practice of the disclosure.

BRIEF DESCRIPTION OF THE DRAWINGS

FIGS. 4A and 4B are a sequence diagram illustrating order of operation of the security labeling service according to an example embodiment.

DETAILED DESCRIPTION

The foregoing and/or other aspects are achieved by providing a Security Labeling Service (SLS) to tag, at runtime, an electronic record or an electronic data stream with a security label. The security label can be applied to any sensitive data which requires access restriction. The use of the security label can thereby ensure proper handling of sensitive data after the data leaves the custodian source.

Figure 1:
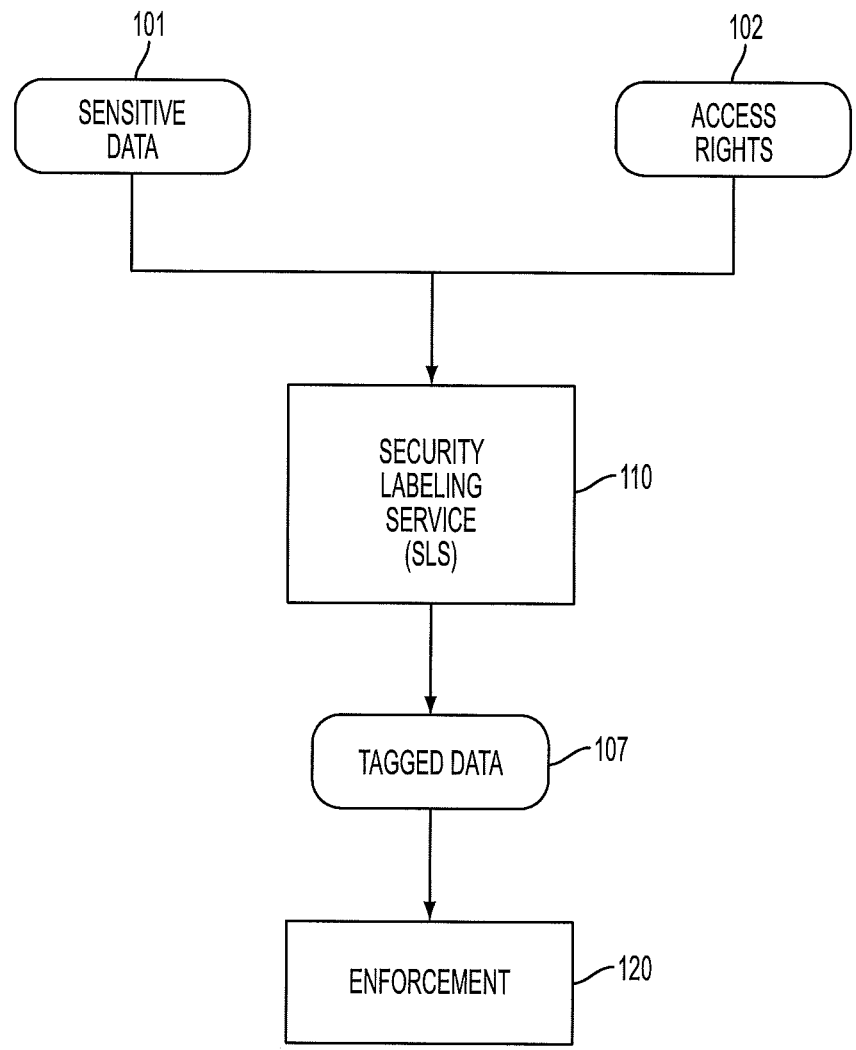
FIG. 1 is a flow chart illustrating tagging data with security labels according to an example embodiment.

FIG. 1 is a flow chart illustrating tagging of data. Sensitive data 101 and access rights 102 are input into the SLS 110. The sensitive data 101 may be in one or more formats expressed according to one or more languages or standards. For example, the sensitive data 101 may be expressed in binary format or some human readable format such as XML. Further, when expressed in, e.g., XML, the sensitive data 101 may be in a specific format requiring a standard use of specific XML tags. However, embodiments are not limited to any particular format.

The SLS 110 interprets the access rights 102 in light of the sensitive data 101 to determine whether any access restrictions apply. The access restrictions may include, for example, redaction, restriction or encryption requirements. However, the scope of access restrictions is not so limited by these examples. If access restrictions from the access rights are applicable to the sensitive data 101, the sensitive data 101 is tagged with security labels by the SLS 110 and output as tagged data 107. The tagged data is then used to ensure automated compliance with access rights 102 by enforcement 120.

Figure 2:
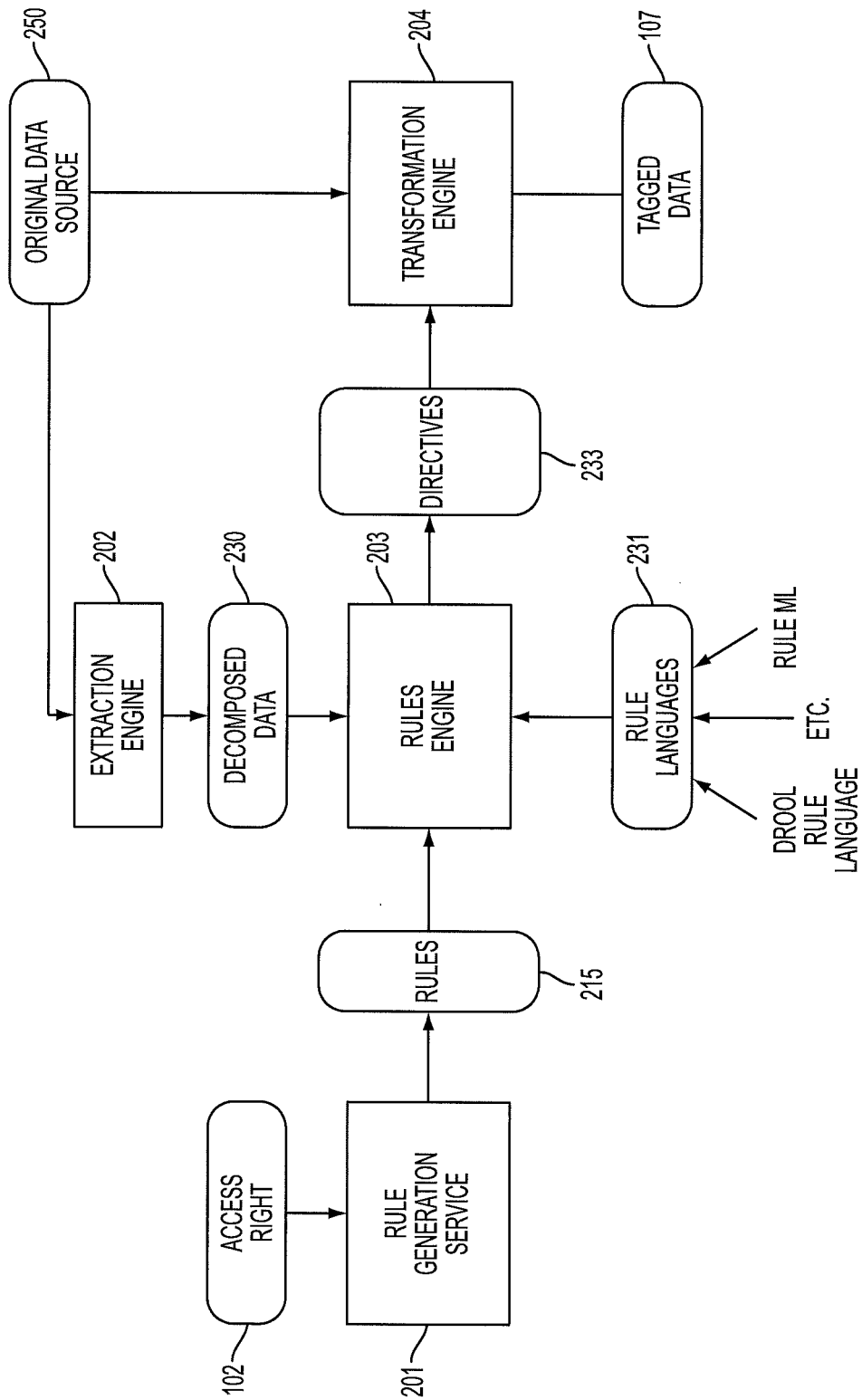
FIG. 2 is a block diagram of a security labeling service for tagging data with security labels according to an example embodiment.

FIG. 2 illustrates an example embodiment of the SLS. The SLS 110 may include a rule generation service 201, an extraction engine 202, a rules engine 203 and a transformation engine 204.

The rule generation service 201 may generate rules 215 based on the access rights 102. The rule generation service 201 outputs rules 215 to the rules engine 203. The rules 215 are a formatted set of access rights 102 which may be expressed in one or more formats that may be recognized by the rules engine 203.

The extraction engine 202 receives an original data source 250. The original data source corresponds to the sensitive data 101, but may be expressed as either an electronic record or an electronic data stream. The extraction engine 202 may have, for example, two basic functions. First, the extraction engine may indicate to the rule generation service what type of electronic records or data stream will be tagged with security labels. For instance, medical records may be stored as a patient's problem list from a HL7 CDA document. The second basic function of the extraction engine is to consume the original data source and decompose the original data source 250 into decomposed data 230 in a standard form which can be interpreted by the rules engine 203. The decomposed data 230 may occur in XML form, for example. However, the scope of the present invention is not limited to XML data. The decomposed data 230 may occur in any form which convenient for the specific implementation as is well known in the art.

The rules engine 203 may receive the decomposed data 230, rules 215, and rule languages 231. The rules 215 may occur in a variety of formats which can be interpreted according to the rule languages 231. The rules engine 203 generates an array or list of required labeling instructions according to the rules 215 which are interpreted according to the rule languages 231 and the decomposed data 230. For example, if only a subset of the rules 215 are applicable to the decomposed data 230, only a subset of the rules 215 are translated to the array or list of required labeling instructions. The array or list of required labeling instructions is then output as directives 233 to the transformation engine 204.

The transformation engine 204 uses the directives 233 output from the rules engine to apply the security label to the original data source 250. The transformation engine 204 then outputs the tagged data 107 as tagged electronic record or electronic data stream which enables automated compliance and enforcement of the constraints of the subject of record authorization, organizational policy, and government regulation.

Figure 3:
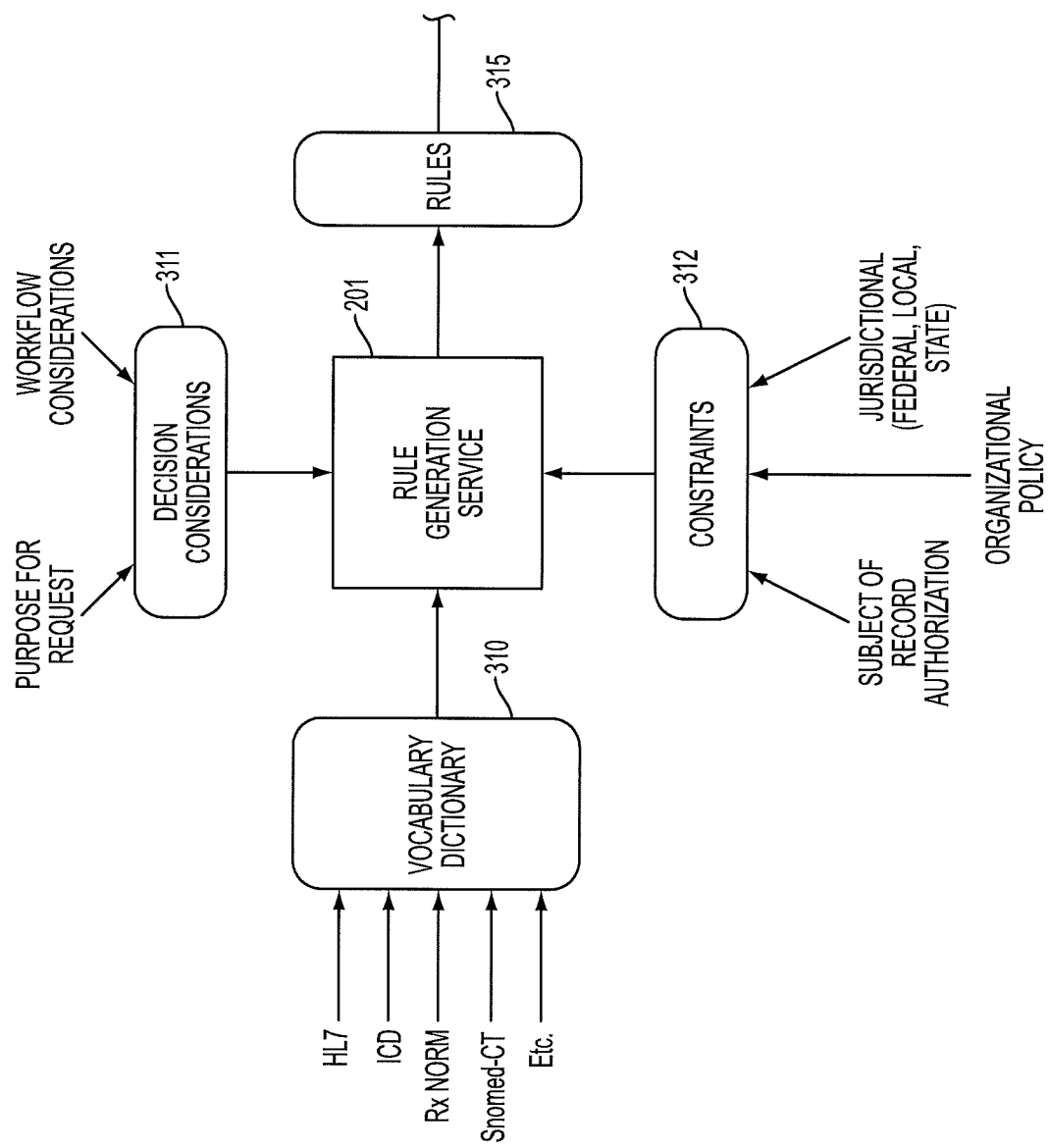
FIG. 3 illustrates the rule generation service portion of the security labeling service in greater detail according to an example embodiment.

FIG. 3 illustrates the rule generation service 201 in greater detail according to an example embodiment. The rule generation service 201 receives a vocabulary dictionary 310, decision considerations 311 and rule constraints 312. The rule constraints 312 represent the access rights 102 expressed in a format which can be interpreted by the rule generation service. The vocabulary dictionary may include vocabulary that can be used to interpret the rule constraints 312. The vocabulary dictionary 310 may include standards generally recognized by an industry. For example, as illustrated in FIG. 3 for the case of medical records, the vocabulary dictionary may include Snomed-CT, RxNorm, ICD, and HL7 terminology. However, this is merely an example, and the vocabulary dictionary may include other standards and languages without departing from the spirit of the present invention.

The rule constraints 312 are a set of access rights which are expressed in a format which can be recognized by the SLS 110. The rule constraints 312 may include, for example, authorization from a subject of record. For example, the authorization from a subject of record could be patient consent for release of medical records that would otherwise not be disclosed. The subject of record authorization may be conditional so that access is permitted only upon satisfying conditions specified by the subject of record.

The rule constraints 312 may further include organizational policy and a government regulation. The government regulation could be, for example, U.S. Privacy Law 42 CFR part 2 which governs medical record privacy. The organizational policy may be additional constraints by an organization which handles the sensitive data, for example, a health care service provider, medical record custodian, or other HIPAA covered entity or business associate. The additional constraints provided by the organizational policy may be, for example, whether to encrypt, mask, or redact records when the records are in transit or at rest.

The rules 215 may be expressed in one or more languages. Also, the rules represent all of the rule constraints 312 without regard to relevance of any sensitive data 101. Therefore, the rules 215 may or may not be applicable to the sensitive data 101 at this stage. Accordingly, as previously indicated, the rules engine 203 outputs a directive 233 which contains only relevant rules.

The decision considerations 311 are a set of conditions which can modify access rights 102 based on the output rules 215. The decision considerations 311 may include, for example, a purpose for request of the sensitive data and also workflow considerations. Taking medical records, again, as an example, the purpose for request may be for treatment, or more specifically, for emergency treatment. Emergency treatment, as opposed to routine treatment such as a physical examination, may allow access to records which would otherwise be redacted from the physician's access. As an alternative example, if the sensitive data 101 is classified information classified as DOD "secret", then the purpose for request may be for designing electronic hardware to meet a specification regarding signal to noise ration of a radio frequency section. In this case, data access may be granted that would otherwise be redacted.

Figure 4A:
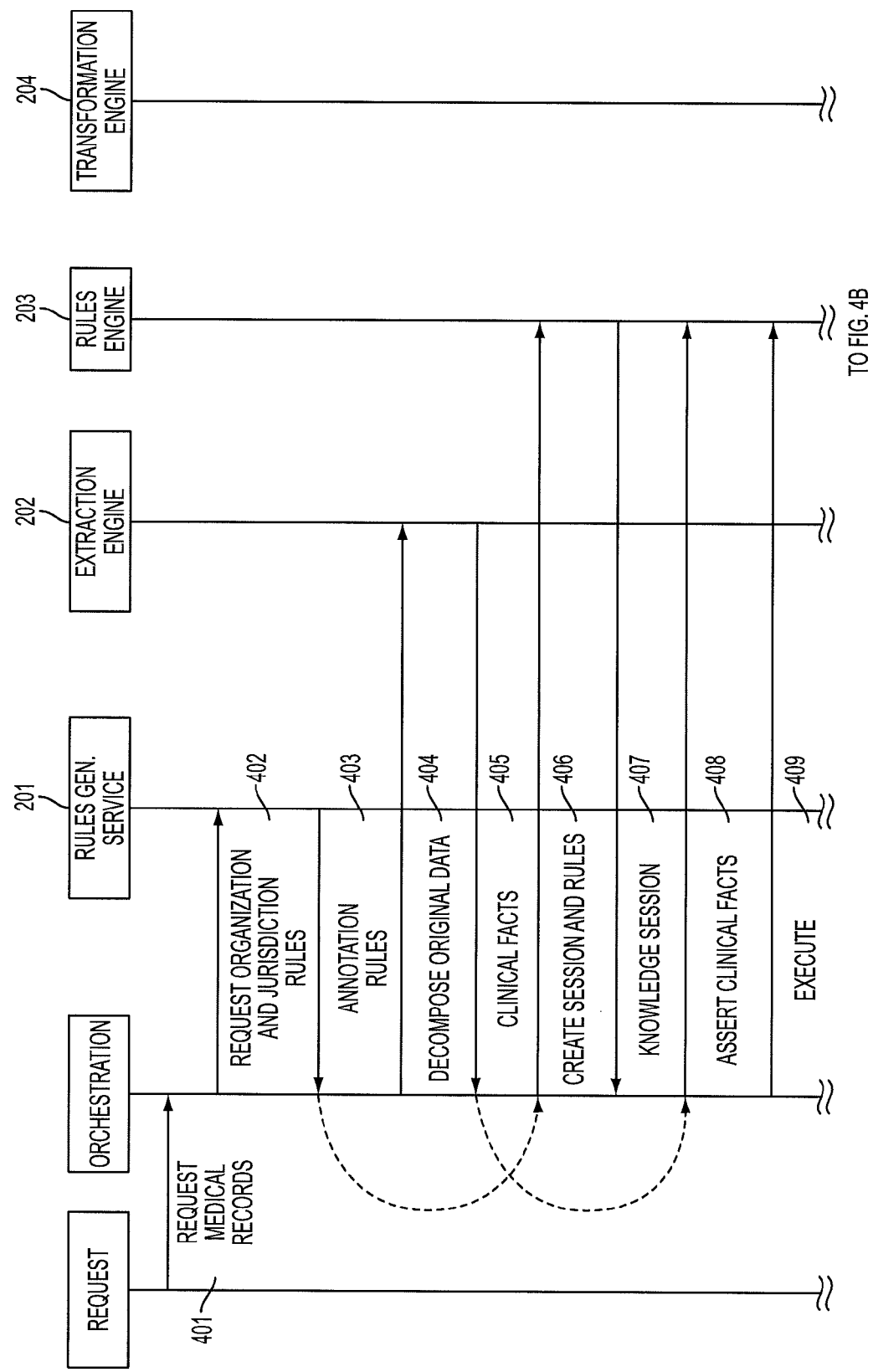

FIGS. 4A and 4B illustrate an example sequence of operations of the SLS 110 in accordance with an exemplary embodiment. The sequence starts at the top of FIG. 4A and ends at the bottom of FIG. 4B which is a continuation of FIG. 4A. The sequence diagram of FIGS. 4A and 4B illustrates the interaction between the SLS 110 components—rule generation service 201, extraction engine 202, rules engine 203, and transformation engine 204—which are depicted horizontally across the top of FIG. 4A. FIGS. 4A and 4B use medical records, again, only as a non-limiting example.

The sequence begins with operation 401 which is a valid request, external to the SLS, for medical records subject to access control. The next two operations involve the rule generation service 201. In operation 402, the SLS 110 retrieves the jurisdictional and policy rules from rules generation service 201. In operation 403, the rule generation service 201 responds to the request by retrieving the rule constraints 312 and generating the annotation rules as rules 215. Note the dotted line which illustrates when the annotation rules next used which is elaborated below.

The next two operations involve the extraction engine 202. In operation 404, the extraction engine 202 decomposes the original data source 250 which is returned in operation 405 as decomposed data 230 which, in the non-limiting example of FIGS. 4A and 4B, includes clinical facts, e.g. a diagnosis containing sensitive information requiring restricted access.

The next five operations involve the rules engine. In operation 406, the annotated rules (or rules 215) are input via the dotted line discussed above, and used to create, in operation 407, a knowledge session in the rules engine 203.

In operation 408, the clinical facts in the decomposed data 230 (from the second dotted line) are asserted in the rules engine 203, and in operation 409, the rules engine is executed to generate the directives 233. In operation 410, the directives are generated.

The next four operations involve the transformation engine. In operation 411, the transformation engine 204 applies the directives 233 to generate, in operation 412, the original data source tagged with security labels. In operation 413, any handling instructions are asserted. The transformation engine responds, in operation 414, by generating the packaged document for transmission.

In operation 420 of FIG. 4B, the tagged data is output from the SLS.

Figure 5:
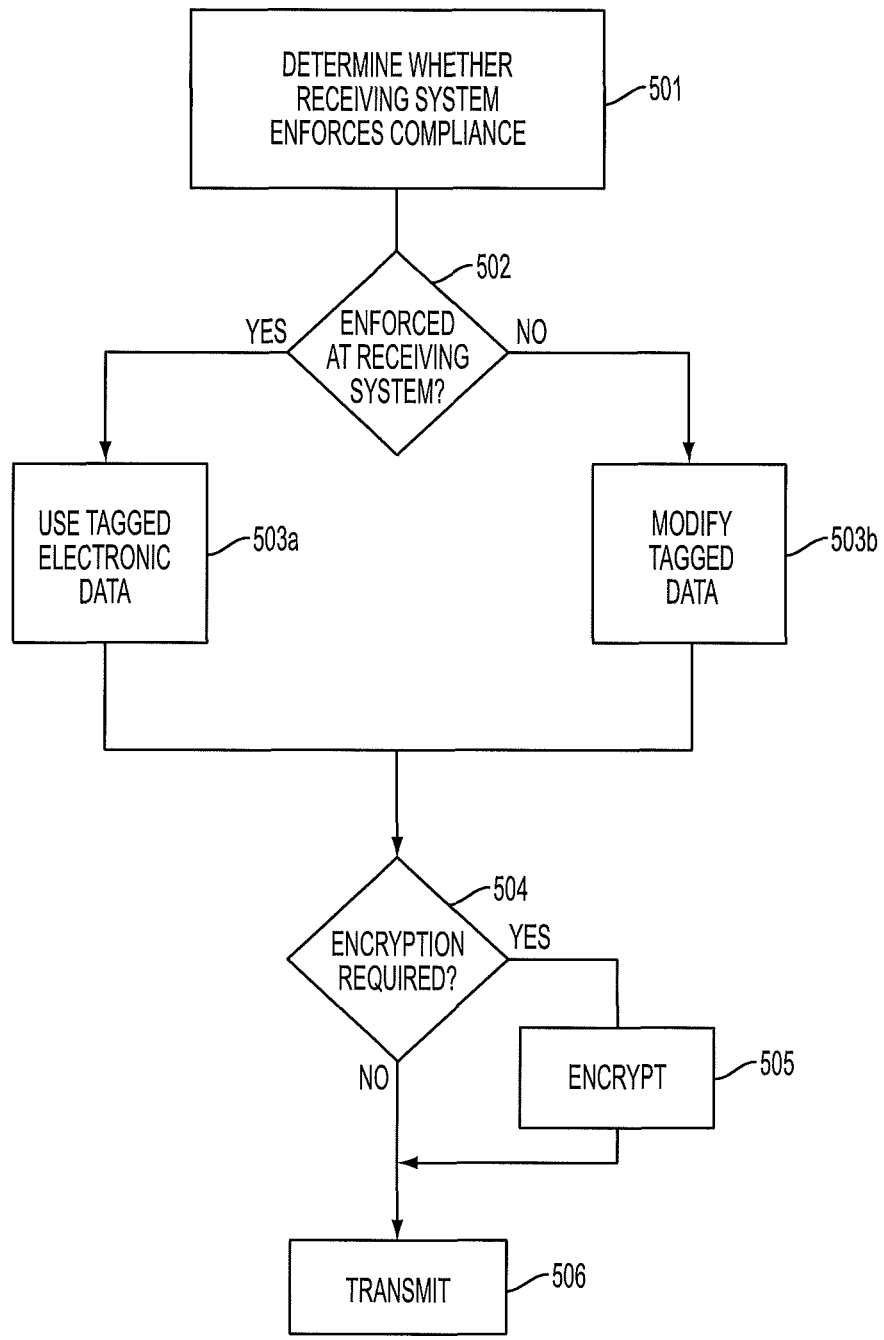
FIG. 5 is a flow chart illustrating a process for automatic compliance with security labels according to an example embodiment.

FIG. 5 illustrates automated compliance with the security labels after data is tagged by the SLS. Note that the illustrations of FIG. 5 do not involve the SLS 110, but rather occur outside the SLS. FIG. 5 represents details of the enforcement 120 of FIG. 1. The tagged data 107, after being tagged with security labels by the SLS 110 is able to ensure automated compliance and enforcement of handling according to the applied security labels when transmitted from a data custodian to any receiving system. Automated compliance may be cooperatively performed in part by the data custodian and in part by the receiving system after the data is tagged with security labels by the SLS 110.

In order for automated compliance to occur, either the data custodian or the receiving system must guarantee the automated compliance. Therefore, before the data is transmitted, the data custodian must determine in operation 501 whether the receiving system is configured to automatically comply with the security labels. At operation 502, a decision is made whether to proceed to operation 503a or 503b. If the receiving system is configured to automatically comply with the security labels, then the tagged data may be sent to the receiving system according to operation 503a. Otherwise, the data custodian must guarantee compliance instead according to operation 503b. For instance, if a record must be redacted, then the data custodian will redact the record according to the tagged security label of tagged data 107 before sending.

Depending on the rule constraints 312 and the transmission medium used to transmit the tagged data 107 from the data custodian to the receiving system, the data may need to be encrypted before and/or after transmission. At decision regarding encryption is performed in operation 504. If encryption is required, the tagged electronic data stream or records will be encrypted in operation 505 before transmission. Encryption may be required according to constraints 112 if transmission occurs, e.g. via the Internet. Encryption might not be required if transmission occurs, e.g. via a local area network (LAN). Encryption requirements will be indicated in the tagged security label.

After automated compliance with the security labels is guaranteed, the data may be transmitted in operation 506 from the data custodian to the receiving party.

Figure 6:
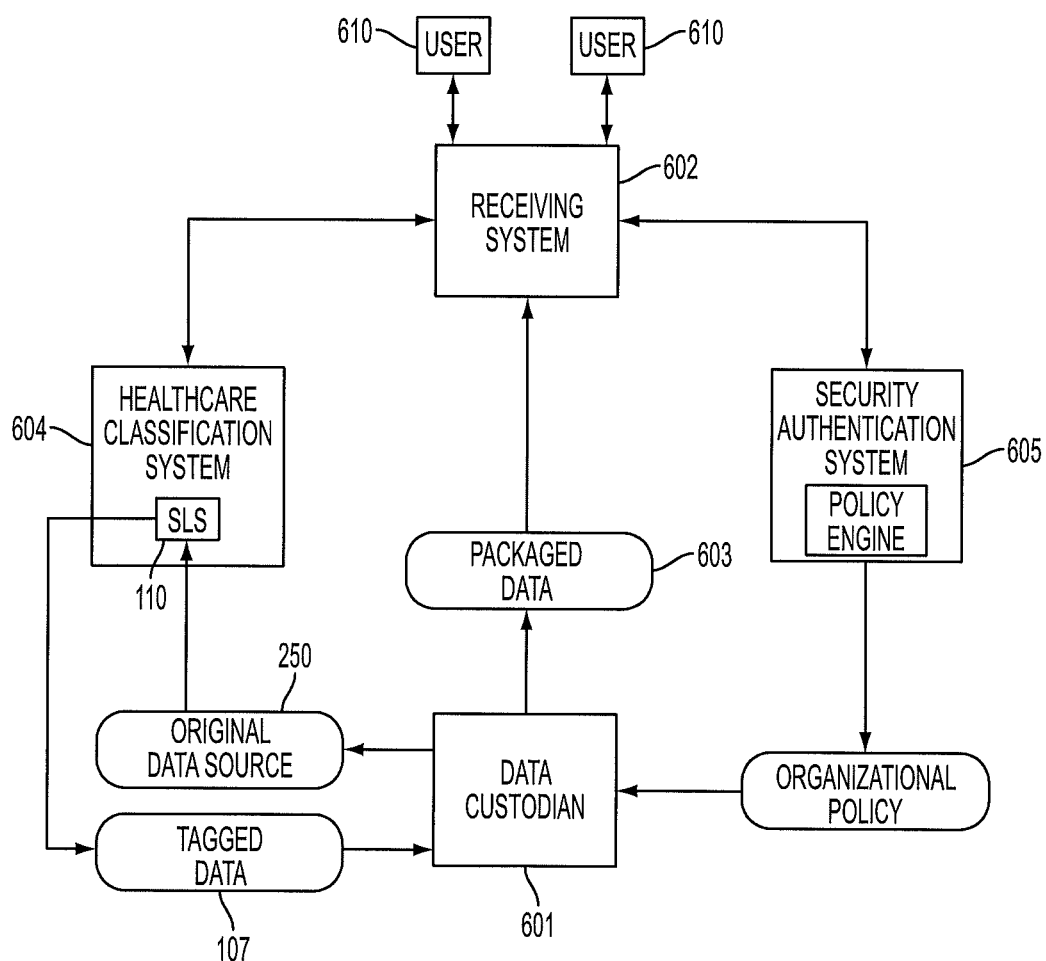
FIG. 6 is a block diagram of a system implementing the security labeling service according to an example embodiment.

FIG. 6 illustrates an exemplary system which incorporates the SLS 110. In this non-limiting example, the data custodian 601 is one health care provider, and the receiving party 602 is another health care provider. The receiving system is accessed by users 610 to request medical records from the data custodian 601. After authentication by the security authentication system 605, the users 610 may request records.

The data custodian accesses the healthcare classification system 604 which hosts the SLS 110. Note that the hosting of the SLS 110 by the healthcare classification system is only a non-limiting example shown for illustrative purposes. Also in this non-limiting example, the organizational policy is retrieved from a policy engine hosted on the security authentication system 605 for use in the SLS 110.

The data custodian 601 uses the SLS 110 to transform original source data 250 into tagged data 107. After ensuring automated compliance, for example, by the illustration of FIG. 5, the data custodian transmits the packaged data 603 to the receiving system for use by the users 610.

The following is an example of input and output data to the SLS 110 in XML format, particularly pertaining to medical records. This is an example of a base rule for a clinical fact pertaining to a medical record, specifically relating to HIV infection which must be restricted according to Federal privacy laws:

```
<ClinicalTaggingRule code="11450-4"
codeSystem="2.16.840.1.113883.5.25"
codeSystemName="LOINC" displayName="Problem List">
    <ClinicalFact code="111880001"
    codeSystem="2.16.840.1.113883.6.96"
    codeSystemName="SNOMED CT" displayName="Acute HIV"/>
    <ActReason code="ETREAT" codeSystem="2.16.840.1.113883.5.8"
    codeSystemName="urn:hl7-org:v3"/>
    <ActInformationSensitivityPolicy code="HIV"
    codeSystem="2.16.840.1.113883.1.11.20429"
    codeSystemName="urn:hl7-org:v3"/>
    <ImpliedConfidentiality>
        Confidentiality code="R"
        codeSystem="2.16.840.1.113883.5.25"
        codeSystemName="urn:hl7-org:v3"/>
    </ImpliedConfidentiality>
</ClinicalTagginRule>
```

The following is another example of another rule, which happens to be expressed in RedHat Drools Rule language, relating to substance abuse:

```
rule "Clinical Rule Substance abuse (disorder) REDACT"
dialect "mvel"
when
    $xacml: XacmlResult(subjectPurposeOfUse=="TREAT", eval(
        pdpObligations.contains(
            "urn:oasis:names:tc:xspa:2.0:recource:patient:redact:ETH")))
    $cd : ClinicalFact(codeSystem == "2.16.840.1.113883.6.96",
            code == "66214007",
            c32SectionLoincCode == "11450-4")
```

```
then
    ruleExecutionContainer.addExecutionResponse(new
        RuleExecutionResponse       ("ETH",
                                    "REDACT",
                                    (String)Confidentiality.R,
                                    "42CRFPart2",
                                    "ENCRYPT",
                                    "NORDSLCD",
                                    $cd.c32SectionTitle,
                                    $cd.c32SectionLoincCode
                                    $cd.observationId,
                                    $cd.code,
                                    $cd.displayName,
                                    "SNOMED CT"))
end
```

The SLS 110 is able to process either of the exemplary above rules because the rules engine 203 uses the rule languages 231 to decode rules 215 which may occur in a plurality of formats and languages.

This is an example of an original data source 250 occurring in XML format, particularly a diagnosis of Acute HIV infection:

```
<?xml version="1.0" encoding="UTF-8"?>
<Problem xmlns="http://hl7.org/fhir">
    <text>
        <status value="generated"/>
        <div xmlns="http://www.w3.org/1999/xhtml">Acute HIV (Date:
21-Nov 2012)</div>
    </text>
    <subject>
        <type value="patient"/>
        <reference value="patient/@example"/>
    </subject>
    <code>
        <text value="AcuteHIV"/>
    </code>
    <category>
        <coding>
            <system value="http://snomed.infor"/>
            <code value="111880001"/>
            <display value="Diagnosis"/>
        </coding>
    </category>
    <status value="confirmed"/>
    <onsetDate value="2012-11-12"/>
</Problem>
```

The SLS 110, according to the above example embodiments, determines that the first of the two above rules is relevant. Accordingly, the SLS 110 tags the above original data source 250 with security labels according to the relevant rule after the rules engine 203 transforms it into a directive 233. The transformation engine 204 outputs:

```
<?xml version="1.0" encoding="UTF-8"?>
<Problem xmlns="http://hl7.org/fhir">
    <text>
        <status value="generated"/>
        <div xmlns="http://www.w3.org/1999/xhtml">Acute HIV (Date:
21-Nov 2012)</div>
    </text>
    <subject>
        <type value="patient"/>
        <reference value="patient/@example"/>
    </subject>
    <code>
        <text value="Acute HIV"/>
    </code>
    <category>
        <coding>
            <system value="http://snomed.infor"/>
            <code value="111880001"/>
            <display value="Diagnosis"/>
        </coding>
    </category>
    <securitylabel>
        <category>
            <term> http://hl7.org/security/../term/restricted</term>
            <label>RESTRICTED</label>
            <scheme>http://hl7.org/security/../confidentiality</scheme>
        </category>
        <category>
            <term>http://hl7.org/security/../term/NORDSLCD</term>
            <label>No Redisclosure with Consent</label>
            <scheme>http://hl7.org/security/../RefrainPolicy</scheme>
        </category>
        <category>
            <term>http://hl7.org/security/../term/ENCRYPT</term>
            <label>ENCRYPT</label>
            <scheme> http://hl7.org/security/../Obligations</scheme>
        </category>
    </securitylabel>
    </category>
    <status value="confirmed"/>
    <onsetDate value="2012-11-12"/>
</Problem>
```

Although many of the foregoing examples specifically involve medical records, the scope of the invention is not limited to medical records. A person having ordinary skill in the art will appreciate that the SLS and other aspects of the present invention can be equally applied to many other forms of sensitive data which require controlled access. As previously indicated, another non-limiting example is the use of the SLS to control access to DOD records, e.g. secret or top secret records. For instance, access may be redacted for a user who has a sufficiently high clearance, but whose purpose for request does not require access to a specific record. Also access may be fully restricted to a user without sufficiently high clearance. Again, these are only non-limiting examples. Further, the present invention is not limited to any particular choice of computer language or format such as the non-limiting examples above which happen to be expressed in XML.

The SLS 110 and other aspects of the foregoing may be implemented in one or more processors or other hardware such as, but not limited to either a programmable gate array or an ASIC. The SLS processing method according to the above-described embodiments of the present invention may be further recorded in non-transitory computer readable media including instructions for controlling one or more processors or other hardware to implement the SLS processing method. The media may include, alone or in combination with the controlling instructions, data files data structures, etc. Non-limiting examples of the non-transitory computer readable media include magnetic media such as hard disks, floppy disks, magnetic tape, etc.; optical media such as CD ROM or DVD disks; magneto-optical media such as floptical disks; and hardware devices that are specifically configured to store and perform program instructions, including but not limited to read only memory (ROM), battery backed up random access memory (RAM), flash memory, etc. Examples of instructions for controlling one or more processors or other hardware include machine code such as produced by a compiler, code in a medium or high level language which may either be compiled (such as C or C++) or executed by a computer using an interpreter (such as JAVA). The various components of the SLS, such as the rule generation service 101, extraction engine 102, rules engine 103, and transformation engine 104 may each be separately implemented in dedicated hardware, or may be implemented together in a single hardware device. For example, the rule generation service 101, extraction engine 102, rules engine 103, and transformation engine 104 may be implemented in at least one computer, or, alternatively, may be implemented in at least one FPGA or ASIC.

Although a few embodiments of the Present Invention have been shown and described, it would be appreciated by those skilled in the art that changes may be made in these embodiments without departing from the principles and spirit of the invention, the scope of which is defined in the claims and their respective equivalents.

What is claimed is:

1. A method comprising:
    by at least one hardware computer:
        receiving, at runtime, a request for an electronic record or electronic data stream from a receiving party;
        receiving the electronic record or electronic data stream from at least one repository in response to the received request;
        dynamically generating, at runtime, a security label according to the electronic record or electronic data stream, information included in the received request, a subject of record authorization, an organizational policy, and a government regulation, the security label corresponding to at least one item included in the received electronic record or electronic data stream and indicating one or a combination of redaction, restriction, and encryption of at least one item included in the received electronic record or electronic data stream;
        inserting, at runtime, the dynamically generated security label into the received electronic record or electronic data stream to generate a tagged electronic record or electronic data stream including the security label and the at least one item corresponding to the security label, thereby enabling automated compliance and enforcement of data handling for each of the subject of record authorization, the organizational policy, and the government regulation according to the information included in the received request, and
        outputting the tagged electronic record or electronic data stream with the inserted security label and the at least one item corresponding to the inserted security label.

2. The method according to claim 1, wherein:
    the security label corresponds to a HL7 Healthcare Classification System (HCS) standard by a Security Labeling System (SLS); and
    the received electronic record or electronic data stream conforms to an HL7 standard that includes Fast Healthcare Interoperability Resources (FHIR) implementations.

3. The method according to claim 2, further comprising:
    by the at least one computer:
        determining whether the receiving party ensures proper compliance with access restrictions according to the HL7 HCS security label and the organizational policy;
        transmitting the tagged electronic record or electronic data stream upon determining that the receiving party ensures proper compliance with the access restrictions; and
        redacting the tagged electronic record or electronic data stream according to the security label and organizational policy upon determining the receiving party does not ensure proper compliance with the access restrictions, and transmitting the redacted tagged electronic record or electronic data stream.

4. The method according to claim 1, further comprising:
    by the at least one computer:
        determining whether the receiving party ensures proper compliance with access restrictions according to the security label and the organizational policy;
        transmitting the tagged electronic record or electronic data stream to the receiving party upon determining the receiving party ensures proper compliance with the access restrictions; and
        redacting the tagged electronic record or electronic data stream according to the security label and organizational policy upon determining the receiving party does not ensure proper compliance with the access restrictions, and transmitting the redacted tagged electronic record or electronic data stream.

5. A method according to claim 1, wherein the received electronic record or electronic data stream is a medical record.

6. A method according to claim 1, wherein the received electronic record or electronic data stream is a record that contains sensitive or classified information.

7. A method according to claim 1, wherein
    the received electronic record or electronic data stream is associated with the subject of record; and
    the inserting further comprises:
        determining a rule for tagging the received electronic record or electronic data stream based on each of the electronic record or electronic data stream, the information included in the received request, the subject of record authorization, the organizational policy, and the government regulation;
        decomposing the received electronic record or electronic data stream into a decomposed data source including the at least one item; and
        generating at least one directive based on a correspondence between the at least one item included in the decomposed data source and the rule for tagging, the at least one directive indicating transformation of the rule for tagging into the security label and indicating the security label is to be inserted into the received electronic record or electronic data stream at a location corresponding to the at least one item; and
        determining an output mode for the outputting of the tagged electronic record or electronic data stream;
    wherein the output mode is one or a combination of storing and transmitting.

8. A method according to claim 7, wherein
    the subject of record is a medical patient;
    the received electronic record or electronic data stream is a medical record; and
    the organizational policy is provided by a health service provider, Health Insurance Portability and Accountability Act (HIPAA) covered entity or business associate, or a record custodian.

9. A method according to claim 8, wherein:
    the determining of a rule for tagging utilizes one or a combination of a vocabulary dictionary and a purpose for requesting the medical record,
    the purpose for requesting the medical record is included in the information included in the received request, and
    the dynamically generating, at runtime, the security label is further according to the purpose for requesting the medical record.

10. A method according to claim 9, wherein the vocabulary dictionary comprises one or a combination of Snomed-CT, RxNorm, International Statistical Classification of Diseases (ICD), HL7, and HL7 HCS.

11. A method according to claim 8, wherein:
at least one of the subject of record authorization, the organizational policy, and the government regulation is expressed in a rule language, and
the rule language comprises one or a combination of Drool Rule Language (DRL) and RuleML; and
the at least one directive indicates the transformation of the rule from the expression in the rule language into the security label expressed in a format of the received electronic record or electronic data stream.

12. A method according to claim 7, further comprising encrypting, by the at least one hardware computer, the tagged electronic record before transmitting.

13. A non-transitory computer readable storage medium containing instructions for controlling one or more hardware processors to implement the method according to claim 1.

14. A method comprising:
by at least one computer:
receiving, at runtime, a retrieval request to retrieve an electronic record associated with a subject of record;
determining a rule for dynamically tagging, at runtime, the electronic record based on the electronic record, information included in the retrieval request, a vocabulary dictionary, an authorization constraint, an organizational policy constraint, and a government rule constraint, to enable automated compliance and enforcement of data handling;
retrieving the electronic record from a repository according to the retrieval request;
decomposing the electronic record into a decomposed data source;
tagging the electronic record at runtime with a security label corresponding to at least one item in the decomposed data source and according to a correspondence between the determined rule and the at least one item in the decomposed data source by inserting the security label into the electronic record to generate a tagged electronic record including the security label and the at least one item corresponding to the security label, the security label indicating one or a combination of redaction, restriction, and encryption of the at least one item as the compliance and enforcement of the data handling according to the information included in the retrieval request; and
outputting the tagged electronic record with the inserted security label and the at least one item corresponding to the inserted security label;
wherein the authorization constraint is provided by the subject of record.

15. A method according to claim 14, wherein:
the electronic record is in XML or JSON format; and
the outputting the tagged electronic record is transmitted within an XML or JSON stream.

16. A method according to claim 15 wherein:
the subject of record is a medical patient;
the electronic record is a medical record of the medical patient
the repository contains electronic records in HL7 standard common data structures and elements or an HL7 Fast Healthcare Interoperability Resources (FHIR) implementation; and
the compliance and enforcement is in accordance with HL7 Healthcare Classification System (HCS).

17. A method according to claim 15, wherein:
a user within an organization corresponding to the organizational policy constraint sends the retrieval request; and
the organizational policy constraint is provided by the organization.

18. A method according to claim 17, wherein
the organization is a health service provider, and
the determining the rule is further based on a purpose for requesting the electronic record included in the information included in the retrieval request.

19. A method according to claim 17, wherein the vocabulary dictionary comprises one or a combination of Snomed-CT, RxNorm, ICD, and HL7, and HL7 HCS.

20. A method according to claim 15, wherein:
one or a combination of the authorization constraint, the organizational policy constraint, and the government rule constraint is expressed in a rule language,
the rule language comprises one or a combination of Drool Rule Language (DRL) and RuleML,
the rule is transformed from the expression in the rule language to a format of the electronic record and inserted as the security label into the electronic record at a location in the electronic record corresponding to the at least one item in the decomposed data corresponding to the determined rule.

21. A method according to claim 15, further comprising encrypting, by the at least one computer, the tagged electronic record before outputting.

22. A method according to claim 15, further comprising enforcing data security according to the security label by an entity sending the retrieval request.

23. An apparatus comprising:
a memory storing instructions;
at least one hardware processor, wherein upon executing the instructions, the at least one hardware processor implements:
a rule generation service configured to dynamically generate, at runtime, a rule from a vocabulary dictionary, rule constraints, decision considerations included in information included in a runtime request to retrieve an electronic record from an original data source, and the electronic record;
an extraction engine configured to transform the electronic record into a decomposed data source;
a rules engine configured to generate, at runtime, a directive from a correspondence between the rule generated by the rule generation service and at least one item in the decomposed data source, the directive indicating how to transform the rule into a security label corresponding to the at least one item in the decomposed data source and indicating where to insert the security label into the electronic record, and the security label indicating at least one of redaction, restriction, and encryption of the at least one item in the decomposed data source according to the rule constraints and the decision considerations included in the information included in the request to retrieve the electronic record from an original data source; and
a transformation engine configured to output an electronic record tagged with the security label by inserting the security label at runtime into the electronic record according to the directive to enable automated compliance and enforcement of data security according to the rule constraints and the decision considerations included in the information included in the request to retrieve the electronic record from an original data source, the tagged electronic record including the security label and a portion of the electronic record corresponding to the at least one item in the decomposed data source corresponding to the security label.

24. An apparatus according to claim 23, further comprising an encryption engine configured to encrypt the electronic record tagged with the security label.

25. An apparatus according to claim 24, wherein the rule constraints comprise an authorization of a subject of record, an organizational policy, and a government rule.

26. An apparatus according to claim 25, wherein:
the subject of record is a medical patient,
the requested electronic record is a medical record associated with the medical patient originating from a HL7 standard common data structure or an HL7 Fast Healthcare Interoperability Resources (FHIR) implementation as the original data source; and
the compliance and enforcement is in accordance with HL7 Healthcare Classification System (HCS).

27. An apparatus according to claim 26, wherein the vocabulary dictionary comprises one or a combination of Snomed-CT, RxNorm, ICD, and HL7, and HL7 HCS.

28. An apparatus according to claim 23, wherein the decision considerations comprise a purpose for requesting the medical record and a workflow consideration.

29. An apparatus according to claim 27, wherein:
rule constraints are expressed in a rule language,
the rule language comprises one or a combination of Drool Rule Language (DRL) and RuleML, and
the directive indicates transformation of the rule expressed in the rule language into the security label expressed in a format of the original data source.

* * * * *

UNITED STATES PATENT AND TRADEMARK OFFICE
CERTIFICATE OF CORRECTION

PATENT NO. : 9,800,582 B2  
APPLICATION NO. : 14/293651  
DATED : October 24, 2017  
INVENTOR(S) : Duane Decouteau et al.

It is certified that error appears in the above-identified patent and that said Letters Patent is hereby corrected as shown below:

In the Claims

Column 11, Line 18:  
In Claim 14, before "computer:" insert -- hardware --.

Column 11, Line 57:  
In Claim 16, after "patient" insert -- ; --.

Signed and Sealed this  
Twentieth Day of February, 2018

Andrei Iancu  
*Director of the United States Patent and Trademark Office*